US006340420B1

(12) United States Patent
Dassel et al.

(10) Patent No.: US 6,340,420 B1
(45) Date of Patent: Jan. 22, 2002

(54) METHODS OF TREATING THE OXIDATION MIXTURE OF HYDROCARBONS TO RESPECTIVE DIBASIC ACIDS

(75) Inventors: Mark W. Dassel, Indianola, WA (US); Eustathios Vassiliou, Newark, DE (US)

(73) Assignee: RPC Inc., Atlanta, GA (US)

( * ) Notice: Subject to any disclaimer, the term of this patent is extended or adjusted under 35 U.S.C. 154(b) by 0 days.

(21) Appl. No.: 09/345,880

(22) Filed: Jun. 30, 1999

Related U.S. Application Data

(60) Provisional application No. 60/091,796, filed on Jul. 6, 1998.

(51) Int. Cl.$^7$ .............................................. B01D 61/44
(52) U.S. Cl. ........................ 204/529; 204/531; 562/440
(58) Field of Search .......................... 562/440; 204/529, 204/531

(56) References Cited

U.S. PATENT DOCUMENTS

| | | |
|---|---|---|
| 1,121,532 A | 12/1914 | Newberry |
| 1,867,933 A | 7/1932 | Wilton |
| 2,014,044 A | 9/1935 | Haswell ........................ 75/17 |
| 2,223,493 A | 12/1940 | Loder ........................ 260/537 |
| 2,223,494 A | 12/1940 | Loder et al. ................ 260/586 |
| 2,301,240 A | 11/1942 | Baumann et al. ........... 183/115 |
| 2,439,513 A | 4/1948 | Hamblet et al. ............ 260/533 |
| 2,557,282 A | 6/1951 | Hamblet et al. ............ 260/533 |
| 2,565,087 A | 8/1951 | Porter et al. ................ 260/631 |
| 2,980,523 A | 4/1961 | Dille et al. .................... 48/215 |
| 3,161,603 A * | 12/1964 | Leyshon et al. |
| 3,231,608 A | 1/1966 | Kollar ........................ 260/533 |
| 3,234,271 A | 2/1966 | Barker et al. ................ 260/531 |
| 3,290,369 A | 12/1966 | Bonfield et al. ............. 260/537 |
| 3,361,806 A | 1/1968 | Lidov ........................ 260/531 |
| 3,386,810 A | 6/1968 | Burke, Jr. et al. ............ 23/285 |
| 3,390,174 A | 6/1968 | Schulz et al. ................ 260/533 |
| 3,515,751 A | 6/1970 | Oberster et al. ............. 260/533 |
| 3,522,018 A | 7/1970 | Bachmann et al. ........... 23/285 |
| 3,530,185 A | 9/1970 | Pugi ............................ 260/586 |
| 3,613,333 A | 10/1971 | Gardenier ...................... 55/89 |
| 3,649,685 A | 3/1972 | Ishimoto et al. ......... 260/533 C |
| 3,677,696 A | 7/1972 | Bryk et al. ...................... 23/2 |

(List continued on next page.)

FOREIGN PATENT DOCUMENTS

| | | |
|---|---|---|
| DE | 2 309 423 | 8/1974 |
| DE | 4426132 A1 | 1/1996 |
| DE | 4427474 A1 | 2/1996 |
| EP | 439 007 A2 | 7/1991 |

(List continued on next page.)

OTHER PUBLICATIONS

E. Sorribes et al., "Formación de nuevas fases on el proceso de obtención de ácido adípico: causas y efectos que provocan," *Rev. R. Acad. Cienc. Exactas, Fis. Nat. Madrid* (1987), 81 (1 ), 233–5 (+English language translation).

Lewis, *Hawley's Condensed Chemical Dictionary*, 12$^{th}$ed., 1993 no month available, pp. 7, 336, and 1076.

Primary Examiner—Arun S. Phasge
(74) Attorney, Agent, or Firm—Seed Intellectual Property Law Group PLLC

(57) ABSTRACT

This invention relates to methods of controlling the oxidation of hydrocarbons to respective dibasic acids, such as adipic acid for example, by removing the catalyst from the reaction mixture, outside the reaction zone, after the oxidation has taken place at least partially. The catalyst is precipitated substantially in its totality by using a base, preferably sodium hydroxide, to form the catalyst hydroxide, such as cobalt hydroxide for example. Preferably, the precipitated catalyst is recycled to the reaction zone with or without further treatment. The method may also include steps for treatment of the reaction mixture by hydrolysis and/or electrodialysis.

34 Claims, 1 Drawing Sheet

FOREIGN PATENT DOCUMENTS

| | | |
|---|---|---|
| EP | 494 416 A2 | 7/1992 |
| EP | 729 084 A1 | 8/1996 |
| EP | 729 085 A1 | 8/1996 |
| EP | 751 105 A2 | 1/1997 |
| FR | 2722783 A1 | 1/1996 |
| GB | 415172 | 8/1934 |
| GB | 738808 | 10/1955 |
| GB | 864106 | 3/1961 |
| GB | 1143213 | 2/1969 |
| GB | 2 014 473 A | 8/1979 |
| GB | 2 072 667 A | 10/1981 |
| JP | 48-003815 | 2/1973 |
| JP | 50034006 B | 11/1975 |
| JP | 54-33891 | 3/1979 |
| JP | 61 063634 | 4/1986 |
| WO | WO 94/07833 | 4/1994 |
| WO | WO 94/07834 | 4/1994 |
| WO | 94-07834 * | 4/1994 |
| WO | WO 96/03365 | 2/1996 |
| WO | WO 96/14288 | 5/1996 |
| WO | WO 96/40610 | 12/1996 |
| WO | WO 97/49485 | 12/1997 |

U.S. PATENT DOCUMENTS

| | | | |
|---|---|---|---|
| 3,819,813 A | 6/1974 | Jones, Jr. et al. | 423/421 |
| 3,839,435 A | 10/1974 | Shigeyasu et al. | 260/524 R |
| 3,869,508 A | 3/1975 | Longley et al. | 260/531 R |
| 3,928,005 A | 12/1975 | Laslo | 55/73 |
| 3,932,513 A | 1/1976 | Russell | 260/586 AB |
| 3,946,076 A | 3/1976 | Paasen et al. | 260/586 P |
| 3,957,876 A | 5/1976 | Rapoport et al. | 260/586 P |
| 3,987,100 A | 10/1976 | Barnette et al. | 260/586 P |
| 3,987,808 A | 10/1976 | Carbonell et al. | 137/3 |
| 4,025,498 A | 5/1977 | Buss et al. | 260/95 A |
| 4,032,569 A | 6/1977 | Onopchenko et al. | 260/533 C |
| 4,039,304 A | 8/1977 | Bechthold et al. | 55/10 |
| 4,055,600 A | 10/1977 | Langley et al. | 260/586 P |
| 4,065,527 A | 12/1977 | Graber | 261/79 A |
| 4,158,739 A | 6/1979 | Schulz et al. | 562/543 |
| 4,160,108 A | 7/1979 | Shigeyasu et al. | 562/416 |
| 4,161,573 A | 7/1979 | Gunsher et al. | 526/64 |
| 4,200,617 A | 4/1980 | Levy | 422/198 |
| 4,263,453 A | 4/1981 | Schulz et al. | 562/543 |
| 4,269,805 A | 5/1981 | Schoengen et al. | 422/106 |
| 4,308,037 A | 12/1981 | Meissner et al. | 55/10 |
| 4,332,590 A | 6/1982 | Smith | 23/230 A |
| 4,361,965 A | 12/1982 | Goumondy et al. | 34/57 R |
| 4,370,304 A | 1/1983 | Hendriks et al. | 422/224 |
| 4,394,139 A | 7/1983 | Board | 55/20 |
| 4,419,184 A | 12/1983 | Backlund | 162/49 |
| 4,423,018 A | 12/1983 | Lester, Jr. et al. | 423/243 |
| 4,477,380 A | 10/1984 | Knips et al. | 260/385 |
| 4,543,399 A | 9/1985 | Jenkins, III et al. | 526/70 |
| 4,588,790 A | 5/1986 | Jenkins, III et al. | 526/70 |
| 4,603,220 A | 7/1986 | Feld | 562/416 |
| 4,902,827 A | 2/1990 | Steinmetz et al. | 562/543 |
| 4,989,452 A | 2/1991 | Toon et al. | 73/293 |
| 5,061,453 A | 10/1991 | Krippl et al. | 422/106 |
| 5,104,492 A | 4/1992 | King et al. | 203/15 |
| 5,117,007 A | 5/1992 | Taheri | 549/259 |
| 5,123,936 A | 6/1992 | Stone et al. | 55/8 |
| 5,139,753 A | 8/1992 | Hardison | 423/220 |
| 5,170,727 A | 12/1992 | Nielsen | 110/346 |
| 5,206,701 A | 4/1993 | Taylor et al. | 356/325 |
| 5,221,800 A | 6/1993 | Park et al. | 562/543 |
| 5,244,603 A | 9/1993 | Davis | 261/87 |
| 5,259,996 A | 11/1993 | Morgan | 261/114.1 |
| 5,270,019 A | 12/1993 | Melton et al. | 422/234 |
| 5,271,904 A | 12/1993 | Esposito et al. | 422/105 |
| 5,286,458 A | 2/1994 | Yang et al. | 422/168 |
| 5,294,378 A | 3/1994 | Succi et al. | 261/130 |
| 5,312,567 A | 5/1994 | Kozma et al. | 261/87 |
| 5,321,157 A | 6/1994 | Kollar | 562/543 |
| 5,374,767 A | 12/1994 | Drinkard et al. | 560/193 |
| 5,396,850 A | 3/1995 | Conochie et al. | 110/346 |
| 5,399,750 A | 3/1995 | Brun et al. | 562/553 |
| 5,463,119 A | 10/1995 | Kollar | 562/543 |
| 5,502,245 A | 3/1996 | Dassel et al. | 562/413 |
| 5,505,920 A | 4/1996 | Kollar et al. | 423/246 |
| 5,516,423 A | 5/1996 | Conoby et al. | 210/85 |
| 5,547,905 A | 8/1996 | Kulsrestha et al. | 502/66 |
| 5,558,842 A | 9/1996 | Vassiliou et al. | 422/108 |
| 5,580,531 A | 12/1996 | Vassiliou et al. | 422/108 |
| 5,654,475 A | 8/1997 | Vassiliou et al. | 562/413 |
| 5,756,837 A | 5/1998 | Costantini et al. | 562/543 |
| 5,801,273 A | 9/1998 | Vassiliou et al. | 562/413 |
| 5,801,282 A | 9/1998 | Dassel et al. | 562/413 |
| 5,817,868 A | 10/1998 | Rostami et al. | 562/413 |
| 5,824,819 A | 10/1998 | Dassel et al. | 562/529 |
| 5,877,341 A | 3/1999 | Vassiliou et al. | 560/77 |
| 5,883,292 A | 3/1999 | Dassel et al. | 562/413 |
| 5,908,589 A | 6/1999 | DeCoster et al. | 264/37.18 |
| 5,922,908 A | 7/1999 | Dassel et al. | 562/543 |
| 5,929,277 A | 7/1999 | DeCoster et al. | 562/593 |
| 6,214,190 B1 * | 4/2001 | Fache et al. | 204/529 |

* cited by examiner

US 6,340,420 B1

METHODS OF TREATING THE OXIDATION MIXTURE OF HYDROCARBONS TO RESPECTIVE DIBASIC ACIDS

CROSS REFERENCE TO RELATED APPLICATIONS

This application claims priority from U.S. Provisional Application No. 60/091,796, filed Jul. 6, 1998, which application is incorporated herein by reference in its entirety.

TECHNICAL FIELD

This invention relates to methods of oxidizing hydrocarbons, such as cyclohexane for example, to respective dibasic acids, such as adipic acid for example, and more specifically, how to remove catalyst after the reaction, preferably for recycling, and how to treat the remaining mixture after removing the catalyst.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase". However, no attention has been paid so far to the importance of the two phases, except for separating the adipic from the "Polar Phase" and recycling these phases to the reactor partially or totally with or without further treatment.

It is also important to note that most studies on the Direct Synthesis-have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of C5–C8 aliphatic dibasic acids by (1) reacting,
 (a) at least one saturated cycloaliphatic hydrocarbon having from 5 to 8 ring carbon atoms in the liquid phase and
 (b) an excess of oxygen gas or an oxygen-containing gas in the presence of
 (c) a solvent comprising an organic acid containing only primary and/or secondary hydrogen atoms and
 (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of C5–C8 aliphatic dibasic acids through oxidation of corresponding saturated cycloaliphatic hydrocarbons by (1) reacting, at a cycloaliphatic hydrocarbon conversion level of between about 7% and about 30%,
 (a) at least one saturated cycloaliphatic hydrocarbon having from 5 to 8 ring carbon atoms in the liquid phase and
 (b) an excess of oxygen gas or an oxygen containing gas mixture in the presence of
 (c) less than 1.5 moles of a solvent per mole of cycloaliphatic hydrocarbon (a), wherein said solvent comprises an organic acid containing only primary and/or secondary hydrogen atoms and
 (d) at least about 0.002 mole per 1000 grams of reaction mixture of a polyvalent heavy metal catalyst; and
(2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 4,680,098 (Chang) describes an electrodialysis method for recovering cobalt or cobalt and manganese from a solution containing oxygenated aromatic compounds.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Obester et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

Patent EP 646 107 A1 (Habermann et al.) discloses a method of producing dicarboxylic acids and diamines by cleavage, with a base, of polymers produced by the dicarboxylic acids and the diamines. The method involves a later step of electrodialysis, in which the dicarboxylic acids are separated and the base formed is recycled.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, control of oxidation reactions by treating the reaction mixture subject to the intricate and critical controls and requirements of the instant invention as described and claimed.

Our U.S. Pat. Nos. 5,654,475, 5,580,531, 5,558,842, 5,502,245, and applications Ser. No. 08/477,195, filed on Jun. 7, 1995 U.S. Pat. No. 5,801,282; and Ser. No. 08/587,967, filed on Jan. 17, 1996 U.S. Pat. No. 5,883,292, all of which are incorporated herein by reference, describe methods and apparatuses relative to controlling reactions in atomized liquids. In addition, the following U.S. applications are also incorporated herein by reference: Ser. No. 08/812,847, filed on Mar. 6, 1997 U.S. Pat. No. 6,288,270; Ser. No. 08/824,992, filed on Mar. 27, 1997 U.S. Pat. No. 5,922,908; Ser. No. 08/859,985 filed on May 21, 1997 U.S. Pat. No. 5,801,273; Ser. No. 08/861,281 filed on May 21, 1997 now abandoned; Ser. No. 08/861,180 filed on May 21, 1997 U.S. Pat. No. 6,103,933; Ser. No. 08/861,176 filed on May 21, 1997 U.S. Pat. No. 5,824,819; Ser. No. 08/859,890 filed on May 21, 1997 U.S. Pat. No. 5,747,233; Ser. No. 08/861,210 filed on May 21, 1997 now abandoned; Ser. No. 08/876,692, filed on Jun. 16, 1997 pending; Ser. No. 08/900,323, filed on Jul. 25, 1997 U.S. Pat. No. 6,037,491; Ser. No. 08/931,035, filed on Sep. 16, 1997 now abandoned; Ser. No. 08/932,875 filed on Sep. 18, 1997 U.S. Pat. No. 6,039,902; Ser. No. 08/934,253, filed on Sep. 19, 1997 U.S. Pat. No. 5,929,277; Ser. No. 08/986,505, filed on Dec. 8, 1997 U.S. Pat. No. 5,908,589; Ser. No. 08/989,910, filed on Dec. 12, 1997 pending; Ser. No. 60/074,068, filed on Feb. 9, 1998; Ser. No. 60/075,257, filed Feb. 19, 1998; Ser. No. 60/086,159, filed May 20, 1998; Ser. No. 60/086,119, filed May 20, 1998; Ser. No. 60/086,118, filed May 20, 1998; and Ser. No. 60/091,483 filed on Jul. 2, 1998, titled "Methods of Recovering Catalyst in Solution in the Oxidation of Cyclohexane to Adipic Acid."

PCT patent application PCT/US97/10830, filed on Jun. 23, 1997 of Mark W. Dassel, David C. DeCoster, Ader M. Rostami, Eustathios Vassiliou, and Sharon M. Aldrich, titled "Methods and Devices for Oxidizing a Hydrocarbon to Form an Acid" is incorporated herein by reference.

Also, PCT patent application PCT/US97/12944, filed on Jun. 23, 1997, of David C. DeCoster, Eustathios Vassiliou, Mark W. Dassel, Sharon M. Aldrich, and Ader M. Rostami, titled "Methods and Devices for Controlling the Reaction Rate and/or Reactivity of Hydrocarbon to an Intermediate Oxidation Product by Adjusting the Oxidant Consumption Rate" is incorporated herein by reference.

SUMMARY OF THE INVENTION

As aforementioned, this invention relates to methods of oxidizing hydrocarbons, such as cyclohexane for example, to dibasic acids, such as adipic acid for example, and more specifically, how to remove catalyst after the reaction, preferably for recycling. More particularly, this invention pertains a method of treating a reaction mixture produced by direct oxidation of hydrocarbon to a respective dibasic acid in a reaction zone, the reaction mixture comprising a monobasic acid solvent having only primary and/or secondary hydrogen atoms, water; and a catalyst, the method being characterized by steps of:

(a) removing a major part of the dibasic acid and a major part of the monobasic acid solvent from the reaction mixture;

(b) adding a base and optionally water into the reaction mixture after it has been treated according to step (a), thus precipitating the hydroxide of the catalyst and forming a salt with any acids present; and (c) removing the hydroxide of the catalyst.

The method may also comprise a step of freeing the acid from the salt by electrodialysis, preferably after hydrolyzing the treated mixture after step (b) or (c). The base used for the hydrolysis may be provided at least partially by the electrodialysis step.

This invention is particularly applicable in the case that the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof. More preferably, the base comprises sodium hydroxide.

The oxygen formed during the electrodialysis may be used as an oxidant for the hydrocarbon, and/or the hydrogen formed during the electrodialysis may be used for energy generation.

Preferably, the catalyst hydroxide is recycled to the reaction zone either directly or after being treated, preferably in a manner to form a solution for easier handling. One type of treatment is by reacting the metal hydroxide, such as cobalt hydroxide with acetic acid to form cobalt acetate.

The method of this invention may further comprise a step of reacting the dibasic acid with a reactant selected from a group consisting of a polyol, a polyamine, and a polyamide in a manner to form a polymer of a polyester, or a polyamide, or a (polyimide and/or polyamideimide), respectively. The polymer may be further spun into fibers. Fillers or other additives may be combined with the polymer or fiber, to form composites.

All ratios and percentages are expressed by weight unless otherwise specified.

A controller, preferably a computerized controller, may handle with ease and accuracy either type of "level." Programming a computerized controller to perform such functions is a routine process, well known to the art. According to this invention, a controller, based on information received, from a reaction zone for example, controls feed rates, temperatures, pressures, and other parameters in order to achieve the desirable results. The controller may also be programmed, by techniques well known to the art, to include flow sheet simulation, which may account for vapor/liquid equilibrium and energy balance effects.

As aforementioned, these methods and devices are particularly suited in case that the hydrocarbon comprises cyclohexane, the mixture comprises acetic acid, and the catalyst comprises a cobalt salt.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

Figure 1:
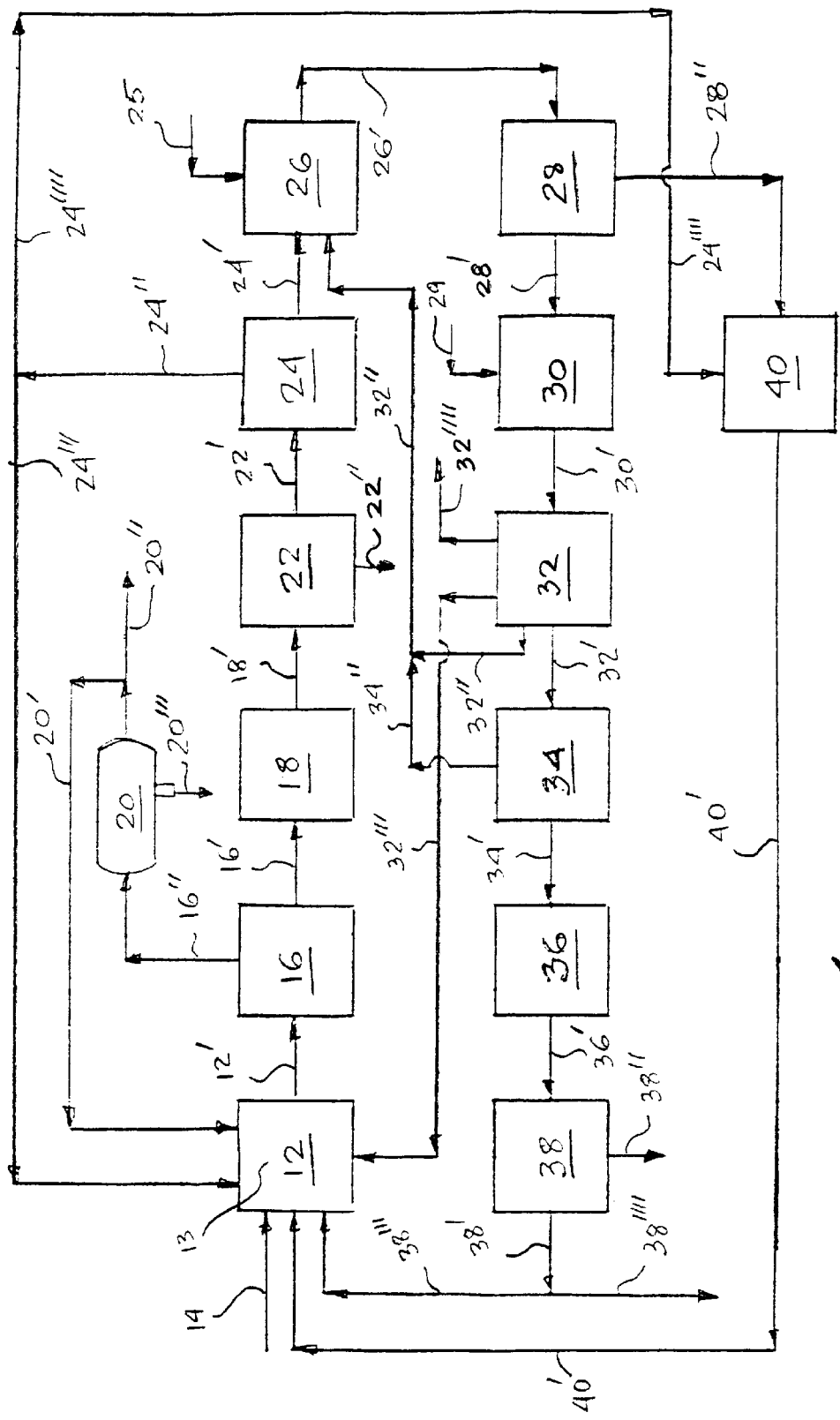
FIG. 1 illustrates a block diagram of a preferred embodiment of the present invention.

As aforementioned, this invention relates to methods and devices for oxidizing hydrocarbons, such as cyclohexane for example, to dibasic acids, such as adipic acid for example, and more specifically, how to remove catalyst after the reaction, preferably for recycling. This invention also relates to methods of treating a reaction mixture in general, so that yields, selectivities, reaction rates, and reactivities are improved.

Proper catalyst handling in oxidation reactions has always been a considerable problem in the art. According to the present invention, catalyst is precipitated substantially in its totality from the reaction mixture after an oxidation has taken place by precipitating it as the hydroxide. This presents enormous advantages, because the precipitated catalyst may be easily and efficiently recycled for repeated utilization.

For better clarification of this invention, the examples given below assume that the hydrocarbon is cyclohexane, the intermediate oxidation product comprises adipic acid, the mixture contains a solvent comprising acetic acid, and the catalyst comprises a cobalt compound. It should be understood, however, that the teachings of this invention are applicable to different hydrocarbons, dibasic acids, solvents, and catalysts than the ones used in the examples. Only minor modifications may be needed to fit each individual case.

Referring now to FIG. 1, there is depicted a reactor system 10 comprising a reaction chamber 12 enclosing a reaction zone 13, and connected to a feeding line 14. The feeding line 14 is shown as a single feeding line for purposes of brevity, simplicity, and clarity, but it represents all feeding lines for introducing reactants and other matter to the reaction chamber 12, as well as heaters, coolers, mixers, etc. for pre-mixing or other treatments of the matter entering the reaction chamber 12. The reaction chamber 12 is a reaction chamber suitable for oxidizing cyclohexane to adipic acid in a direct synthesis. Such reaction chambers have been disclosed in a number of our patents and patent applications, as well as in the relevant art. The reaction chamber 12 may be a stirred tank reaction chamber, atomization reaction chamber, recirculation reaction chamber, or any other type of reaction chamber known to the art. Miscellaneous accessories to the reaction chamber are not shown for purposes of brevity and clarity. Such accessories, however, may be condensers, decanters, heating or cooling devices, such as coils for example, etc. The reaction chamber 12 is also connected to a first evaporator 16 through line 12', which first evaporator is not absolutely necessary, but nevertheless it is highly desirable.

The first evaporator 16 is connected to a first cooler or crystallizer 18 through line 16', and to a decanter 20 through line 16". The decanter is connected back to the reaction chamber 12 through a non-polar phase recycle line 20', to a non-polar purge line 20", and to a polar phase line 20'''.

The first cooler or crystallizer 18 is connected to a first solids separator 22, which is connected to a second evaporator 24, which while is not absolutely necessary, it is nevertheless highly desirable. The first cooler ox crystallizer 18 is also connected to a dibasics removal line 22".

The second evaporator 24 is connected to a catalyst precipitator 26 through line 24' and to a distillate line 24". The distillate line 24" is in turn connected to line 24''', which leads to the reaction chamber 12, and/or to line 24'''', which leads to a catalyst treatment section 40.

The catalyst precipitator 26 is connected to a second solids separator 28 through line 26'. An inlet line 25 is also connected to the catalyst precipitator 26 for addition of matter, if needed.

The second solids separator 28 is connected to a hydrolysis section 30 through line 28', and to catalyst treatment section 40 through catalyst removal line 28".

The catalyst treatment section 40 is in turn connected to the reaction chamber 12 through line 40'. In case that a catalyst treatment section is not used, the catalyst removal line 28" is preferably connected directly to the reaction chamber 12.

The hydrolysis section 30 is connected to an electrodialysis section 32 through line 30'. An inlet 29 is also connected to the hydrolysis section 30 for addition of matter, if needed. Electrodialysis devices are well known to the art (see for example, U.S. Pat. No. 4,680,098 and DE 4,219,757, which are incorporated herein by reference).

The hydrolysis section 30 may be combined with catalyst precipitator 26. In such a case, the second solids separator 28 may be connected directly to the electrodialysis section.

The electrodialysis section 32 is connected to a third evaporator 34 through line 32'. The electrodialysis section 32 is also connected to the catalyst precipitator 26 through hydroxide recycle line 32", to the reaction chamber 12 through oxygen carrying line 32''', and to hydrogen line 32''''. The hydrogen line is preferably connected (not shown) to any appropriate device needing energy and can use hydrogen to retrieve said energy.

The third evaporator 34 is connected to a second cooler or crystallizer 36 through line 34'.

The cooler or crystallizer 36 is connected to a third solids separator 38 through line 36'.

The third solids separator 38 is connected to a dibasics removal line 38', and to a line 38' which leads to the reaction chamber 12 through line 38", and to a purge line 38'''.

In operation of this embodiment, raw materials and other matter required for the oxidation of cyclohexane to adipic acid enter the reaction chamber 12 through feeding line 14. Feeding line 14 represents more than 1 line through which the feeding occurs, but it is shown as a single line for purposes of clarity and brevity. In an example of the direct oxidation of cyclohexane to adipic acid, the cyclohexane is oxidized by oxygen in the presence of a monobasic acid solvent, such as acetic acid for example, a catalyst, such as a cobalt compound for example, and an initiator, such as cyclohexanone or acetaldehyde for example. Oxygen may be provided to the reaction chamber 12 either through line 14 or through line 32" or through both. This also depends on the amount of oxygen liberated during the electrodialysis.

The reaction mixture from the reaction chamber 12 is lead to the first evaporator 16, where it is concentrated in order to improve quantitywise the precipitation or crystallization of the dibasic acid, such as adipic acid for example in the cooler or crystallizer 18. The distillate from the first evaporator 16 is lead through a condenser (not shown) to the decanter 20, in which it is separated into a polar phase containing mainly monobasic acid solvent, such as acetic acid for example, and water, and a non-polar phase containing mainly hydrocarbon, such as cyclohexane for example. The hydrocarbon is preferably recycled to the reaction chamber 12 through line 20', while part of the hydrocarbon may be purged through line 20", if so desired. The polar phase may be recycled or otherwise treated, depending on the circumstances.

The first evaporator 16 is not absolutely necessary, since dibasic acid, such as adipic acid for example, precipitates or crystallizes to a certain degree at the low temperatures prevailing in the cooler 18. However, the use of the evaporator 16 is highly desirable in order to maximize the degree of precipitation or crystallization of the dibasic acid, such as adipic acid for example.

The suspension of dibasic acid, such as adipic acid for example, is lead to the first solids separator 22. Examples of solids separators are centrifugal separators, filtering devices, etc. the dibasic acid is thus, separated and removed through line 22". An additional crystallization from water or acetic acid or other vehicle may be conducted in an additional section (not shown) in order to purify the dibasic acid.

The remaining liquid after the removal of the dibasic acid, such as adipic acid for example, is lead to a second evaporator 24, where the majority of the monobasic acid solvent, such as acetic acid for example, is evaporated, preferably under 100° C., and more preferably in the range of 50–100° C., preferably under vacuum, leaving behind a mixture of dibasic acids, esters, and miscellaneous other moieties. The evaporated monobasic acid solvent is preferably recycled partially to the reaction chamber 12 through the sequence of lines 24" and 24''', and partially to the catalyst treatment section 40, if such a section is utilized. A base, preferably selected from the groups of alkalis and/or alkaline earths is added to the catalyst precipitator. Most of the base is provided by recycling an aqueous solution of the base from the electrodialysis section 32 through line 32", while complementary base and/or water may be added through inlet 25. The base, preferably sodium hydroxide, precipitates the catalyst as the hydroxide of catalyst, such as $Co(OH)_2$ for example, which is insoluble in water for all practical purposes. The solubility of $Co(OH)_2$ in cold water is about 0.00032 gram per 100 cc of water. The amount of base in the catalyst precipitator 26 should preferably be high enough to precipitate substantially all the catalyst in the hydroxide form, and also neutralize all acids present. It may also be even higher in a manner to cause hydrolysis at this or at a later step.

The slurry containing the precipitated catalyst as catalyst hydroxide is lead to the second solids separator 28 through line 26', wherein the catalyst hydroxide is separated and removed through line 28", which preferably leads to the catalyst treatment section 40. In the absence of the catalyst treatment section 40, line 28" may lead directly to the reaction chamber 12, following the path of line 40'. The existence of the catalyst treatment section 40 is preferable, since the insoluble catalyst hydroxide may readily form a soluble salt, such as cobalt acetate for example. As aforementioned, a part of the monobasic acid solvent, such as acetic acid for example, may be added to the catalyst treatment section 40 through line 24"". Water may also be added to the catalyst treatment section 40 through an inlet line (not shown). After the catalyst hydroxide has been solubilized as a salt, it is preferably transferred t(o the reaction chamber 12 through line 40'.

The liquid separated from the catalyst hydroxide in the second solids separator 28 is lead to the hydrolysis section 30. If a high enough metal (alkali or alkaline earth) hydroxide has been added to the catalyst precipitator to result in an efficient hydrolysis of ester in the hydrolysis section 30, no further addition of metal hydroxide is needed. If, however, more metal hydroxide is needed, it may be added through inlet 29. After the hydrolysis, substantially water insoluble liquids, such as cyclohexanol for example, are removed by decanting (not shown).

After hydrolysis of the esters, the hydrolyzed liquid enters the electrodialysis section 32. In the electrodialysis section 32, the salts present after the hydrolysis section 30 are separated into mostly free acids towards the anodic section, and mostly free base toward the cathodic section, in aqueous solutions. The aqueous solution of the base, sodium hydroxide for example, is recycled to the catalyst precipitator 26 through line 32". In the catalyst precipitator 26, it causes catalyst, such as a cobalt salt for example, to precipitate in the form of the hydroxide. As aforementioned, complementary base and/or water may be added to the catalyst precipitator 26 through inlet 25.

The hydrolysis step and the catalyst precipitation step may be conducted in the catalyst precipitator 26, in which case, the hydrolysis chamber 30 is not needed.

Oxygen which may be formed in the anode of the electrodialysis section is preferably directed to the reaction chamber 12 through line 32'" to be used as oxidant for the hydrocarbon, such as cyclohexane for example. Hydrogen which may be formed at the cathode of electrodialysis section is directed to any section of the reactor device 10, or to any other station outside the reactor device 10, for producing energy or any other useful purpose.

The aqueous solution of the free acids is transferred to the third evaporator 34, where a desirable amount of water is removed, and the solution is concentrate to a point that after being transferred to the second cooler or crystallizer 36 through line 34', more dibasic acid, such as adipic acid for example, is precipitated. The precipitated dibasic acid is removed through line 38' connected to the third solids separator 38. The distillate from the third evaporator 34, comprising mainly water, may be returned to the catalyst precipitator 26 through line 34", or it may be used otherwise.

The liquids remaining after removal of the precipitated dibasic acid are recycled to the reaction chamber 12 through the sequence of lines 38' and 38'", and/or purged through the sequence of lines 38' and 38"".

The dibasic acid, such as adipic acid for example, separated by the first solids separator 22 and the third solids separator 38 may need recrystallization, preferably from water, and more preferably from the monobasic acid solvent, such as acetic acid for example.

The precipitated catalyst, such as cobalt hydroxide for example, separated by the second solids separator 28, is preferably washed with water, which water may then be recycled (not shown) to the catalyst precipitator 26.

It should be understood that according to the present invention, any liquids or gases or off-gases may be recycled totally or partially from any section to any other section, if so desired. Further, any combinations of the exemplifying embodiments, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of C5–C8 aliphatic dibasic acids from the corresponding saturated cycloaliphatic hydrocarbons, such as for example preparation of adipic acid from cyclohexane. Examples of aromatic carboxylic acids are benzoic acid, phthalic acid, isophthalic acid, and terephthalic acid, among others.

Regarding adipic acid, the preparation of which is especially suited to the methods and apparatuses of this invention, general information may be found in a plethora of U.S. Patents, among other references. These include, but are not limited to: U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); U.S. Pat. Nos. 4,263,453; 4,331,608; 4,606,863; 4,902,827; 5,221,800; and 5,321,157.

Diacids (for example, adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers. Fillers and/or other additives may be combined with the polymer or fiber so as to form composites.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

What is claimed is:

1. A method of treating a reaction mixture produced by direct oxidation of hydrocarbon to a respective dibasic acid in a reaction zone, the reaction mixture comprising a monobasic acid solvent having only primary and/or secondary hydrogen atoms, water, and a catalyst, the method being characterized by steps of:
   (a) removing a major part of the dibasic acid and a major part of the monobasic acid solvent from the reaction mixture;
   (b) adding a base and optionally water into the reaction mixture after it has been treated according to step (a), thus precipitating the hydroxide of the catalyst and forming a salt with any acids present; and
   (c) removing the hydroxide of the catalyst.

2. A method as defined in claim 1, further comprising a step of hydrolyzing the treated mixture during or after step (b), or after step (c).

3. A method as defined in claim 2 wherein the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof.

4. A method as defined in claim 3 wherein the catalyst hydroxide is recycled to the reaction zone either directly or after being treated.

5. A method as defined in claim 2 wherein the catalyst hydroxide is recycled to the reaction zone either directly or after being treated.

6. A method as defined in claim 1 wherein the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof.

7. A method as defined in claim 6 wherein the catalyst hydroxide is recycled to the reaction zone either directly or after being treated.

8. A method as defined in claim 1 wherein the catalyst hydroxide is recycled to the reaction zone either directly or after being treated.

9. A method as defined in claim 1, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

10. A method as defined in claim 9, further comprising a step selected from a group consisting of spinning the polymer into fibers, adding to the polymer fillers and/or other additives to form composites, and a combination thereof.

11. A method of treating a reaction mixture produced by direct oxidation of hydrocarbon to a respective dibasic acid in a reaction zone, the reaction mixture comprising a monobasic acid solvent having only primary and/or secondary hydrogen atoms, water, and a catalyst, the method being characterized by steps of:
   (a) removing a major part of the dibasic acid and a major part of the monobasic acid solvent from the reaction mixture;
   (b) adding a base and optionally water into the reaction mixture after it has been treated according to step (a), thus precipitating the hydroxide of the catalyst and forming a salt with any acids present;
   (c) removing the hydroxide of the catalyst; and
   (d) freeing the acid from the salt by electrodialysis.

12. A method as defined in claim 11, further comprising a step of hydrolyzing the treated mixture during or after step (b), or after step (c).

13. A method as defined in claim 12 wherein the base is provided by the electrodialysis step.

14. A method as defined in claim 13 wherein the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof.

15. A method as defined in claim 14 wherein oxygen formed during the electrodialysis is used as an oxidant for the hydrocarbon, and/or hydrogen formed during the electrodialysis is used for energy generation.

16. A method as defined in claim 13 wherein oxygen formed during the electrodialysis is used as an oxidant for the hydrocarbon, and/or hydrogen formed during the electrodialysis is used for energy generation.

17. A method as defined in claim 12 wherein oxygen formed during the electrodialysis is used as an oxidant for the hydrocarbon, and/or hydrogen formed during the electrodialysis is used for energy generation.

18. A method as defined in claim 17 wherein the catalyst hydroxide is recycled to the reaction zone either directly or after being treated.

19. A method as defined in claim 12 wherein the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof.

20. A method as defined in claim 19 wherein oxygen formed during the electrodialysis is used as an oxidant for the hydrocarbon, and/or hydrogen formed during the electrodialysis is used for energy generation.

21. A method as defined in claim 11 wherein the base is provided by the electrodialysis step.

22. A method as defined in claim 21 wherein the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof.

23. A method as defined in claim 22 wherein oxygen formed during the electrodialysis is used as an oxidant for the hydrocarbon, and/or hydrogen formed during the electrodialysis is used for energy generation.

24. A method as defined in claim 21 wherein oxygen formed during the electrodialysis is used as an oxidant for the hydrocarbon, and/or hydrogen formed during the electrodialysis is used for energy generation.

25. A method as defined in claim 11 wherein the hydrocarbon comprises cyclohexane, the dibasic acid comprises adipic acid, the monobasic acid solvent comprises acetic acid, the catalyst comprises a cobalt compound, and the base is selected from a group consisting of alkali metal hydroxide, alkaline earth hydroxide, and a mixture thereof.

26. A method as defined in claim 25 wherein oxygen formed during the electrodialysis is used as an oxidant for the hydrocarbon, and/or hydrogen formed during the electrodialysis is used for energy generation.

27. A method as defined in claim 25 wherein the catalyst hydroxide is recycled to the reaction zone either directly or after being treated.

28. A method as defined in claim 11 wherein oxygen formed during the electrodialysis is used as an oxidant for the hydrocarbon, and/or hydrogen formed during the electrodialysis is used for energy generation.

29. A method as defined in claim 28 wherein the catalyst hydroxide is recycled to the reaction zone either directly or after being treated.

30. A method as defined in claim 11 wherein oxygen is formed during the electrodialysis at the anode, and hydrogen is formed at the cathode.

31. A method as defined in claim 30 wherein the catalyst hydroxide is recycled to the reaction zone either directly or after being treated.

32. A method as defined in claim 11 wherein the catalyst hydroxide is recycled to the reaction zone either or after being treated.

33. A method as defined in claim 11, further comprising a step of reacting the acid with a reactant selected from a group consisting of a polyol, a polyamine, and a polyamide in a manner to form a polymer of a polyester, or a polyamide, or a (polyimide and/or polyamideimide), respectively.

34. A method as defined in claim 33, further comprising a step of spinning the polymer into fibers.

* * * * *

UNITED STATES PATENT AND TRADEMARK OFFICE
CERTIFICATE OF CORRECTION

PATENT NO. : 6,340,420 B1
DATED : January 22, 2002
INVENTOR(S) : Mark W. Dassel and Eustathios Vassiliou It is certified that error appears in the above-identified patent and that said Letters Patent is hereby corrected as shown below:

<u>Column 14,</u>
Line 19, "zone either or after" should be corrected to read -- zone either directly or after --.

Signed and Sealed this

Twentieth Day of August, 2002

Attest:

Attesting Officer

JAMES E. ROGAN
*Director of the United States Patent and Trademark Office*